United States Patent
Daglow

(10) Patent No.: US 7,567,842 B1
(45) Date of Patent: Jul. 28, 2009

(54) HOUSING PROVIDING AN ELECTRICAL STIMULATION LEAD CONTACT IN AN IMPLANTABLE STIMULATION DEVICE

(75) Inventor: Terry D. Daglow, Allen, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 311 days.

(21) Appl. No.: 11/536,393

(22) Filed: Sep. 28, 2006

Related U.S. Application Data

(60) Provisional application No. 60/721,878, filed on Sep. 29, 2005.

(51) Int. Cl.
*A61N 1/372* (2006.01)

(52) U.S. Cl. ........................................................ 607/37

(58) Field of Classification Search .................. 607/36, 607/37
See application file for complete search history.

(56) References Cited

U.S. PATENT DOCUMENTS

2004/0093038 A1* 5/2004 Biggs et al. ................... 607/37

* cited by examiner

*Primary Examiner*—Scott M Getzow
(74) *Attorney, Agent, or Firm*—Christopher S. L. Crawford; Peter Lando; Melissa Acosta

(57) ABSTRACT

One embodiment includes a tubular housing for electrically connecting an implantable stimulation device to an implantable electrical stimulation lead. The tubular housing includes a tubular outer segment including a first material, a tubular middle segment inside the outer segment in contact with the outer segment including a second material, and a tubular inner segment inside the middle segment in contact with the middle segment including a third material. A circumferential groove in the inner segment exposes a portion of the middle segment to an axial hole through the tubular housing. The groove is adapted to receive a coiled spring. The groove enables transmission of stimulation pulses from the exposed portion of the middle segment, through the coiled spring, to the stimulation lead inserted through the axial hole for stimulation of tissue in a patient.

20 Claims, 4 Drawing Sheets

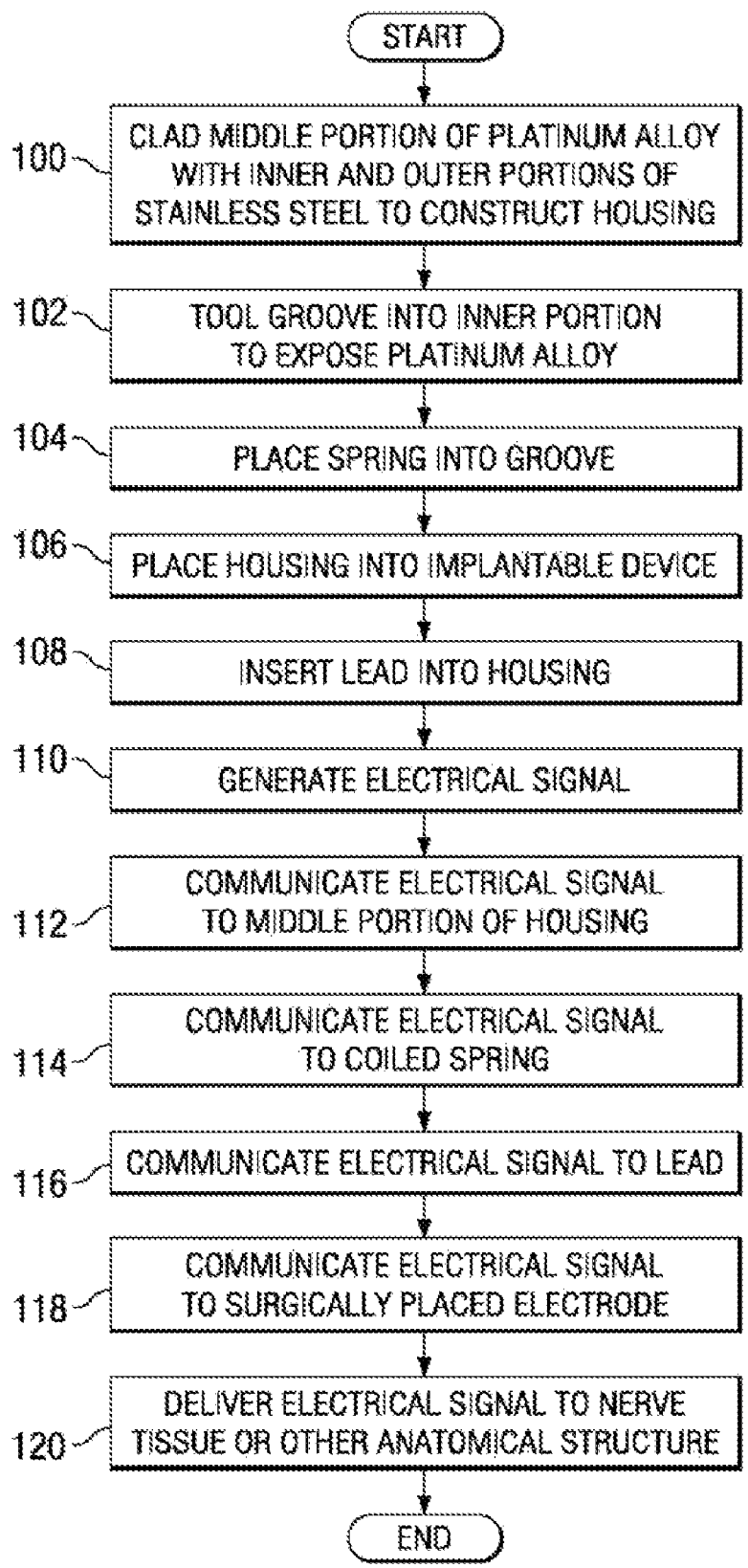

HOUSING PROVIDING AN ELECTRICAL STIMULATION LEAD CONTACT IN AN IMPLANTABLE STIMULATION DEVICE

CROSS-REFERENCE TO RELATED APPLICATIONS

This application claims the benefit of U.S. Provisional Application Ser. No. 60/721,878 filed Sep. 29, 2005, entitled "HOUSING PROVIDING AN ELECTRICAL STIMULATION LEAD CONTACT IN AN IMPLANTABLE NEUROSTIMULATION DEVICE," which is incorporated herein by reference.

TECHNICAL FIELD

This application relates generally to implantable neurostimulation devices and more particularly to a housing providing an electrical stimulation lead contact in an implantable neurostimulation device.

BACKGROUND

An implantable neurostimulation device includes a housing for receiving a proximal end of an implantable electrical stimulation lead and electrically connecting the circuitry of the device to appropriate components of the stimulation lead to enable stimulation of tissue in a patient. The housing includes electrical contacts corresponding to terminal electrodes located along the proximal end of the stimulation lead. The terminal electrodes are connected to corresponding stimulation electrodes located along the distal end of the stimulation lead via wires running through the stimulation lead. Electrical stimulation pulses are generated at the device and transmitted through the electrical contacts, terminal electrodes, wires, and stimulation electrodes to the tissue to be stimulated. A typical electrical contact for such a device is made of platinum or an alloy of approximately 90% platinum and approximately 10% iridium. Platinum is expensive, but resistant to oxidation and corrosion that may adversely affect electrical connectivity between the electrical contact and the corresponding terminal electrode of the stimulation lead.

SUMMARY

According to some embodiments, disadvantages and problems associated with previous structures for providing electrical connectivity between an implantable neurostimulation device and an implantable electrical stimulation lead may be reduced or eliminated.

One embodiment includes a tubular housing for electrically connecting an implantable neurostimulation device to an implantable electrical stimulation lead. The tubular housing includes a tubular outer segment including a first material, a tubular middle segment inside the outer segment in contact with the outer segment including a second material, and a tubular inner segment inside the middle segment in contact with the middle segment including a third material. A circumferential groove in the inner segment exposes a portion of the middle segment to an axial hole through the tubular housing. The groove is adapted to receive a coiled spring. The groove enables transmission of stimulation pulses from the exposed portion of the middle segment, through the coiled spring, to the stimulation lead inserted through the axial hole for neurostimulation of tissue in a patient.

Particular embodiments of the present invention may provide one or more technical advantages. For example, particular embodiments may reduce an amount of platinum needed for an electrical contact of the neurostimulation device while retaining one or more benefits of using platinum (such as resistance to oxidation and corrosion) for the electrical contact. Certain embodiments of the present invention may provide all, some, or none of these technical advantages. Certain embodiments may provide one or more other technical advantages, one or more of which may be readily apparent to those skilled in the art from the figures, description, and claims herein.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

BRIEF DESCRIPTION OF THE DRAWINGS

To provide an understanding of some embodiments and features and advantages thereof, reference is made to the following description taken in conjunction with the accompanying drawings, in which:

FIG. 8 illustrates an example method for reducing an amount of a contact material for an electrical stimulation lead contact in an implantable neurostimulation device.

DETAILED DESCRIPTION

Figure 1:
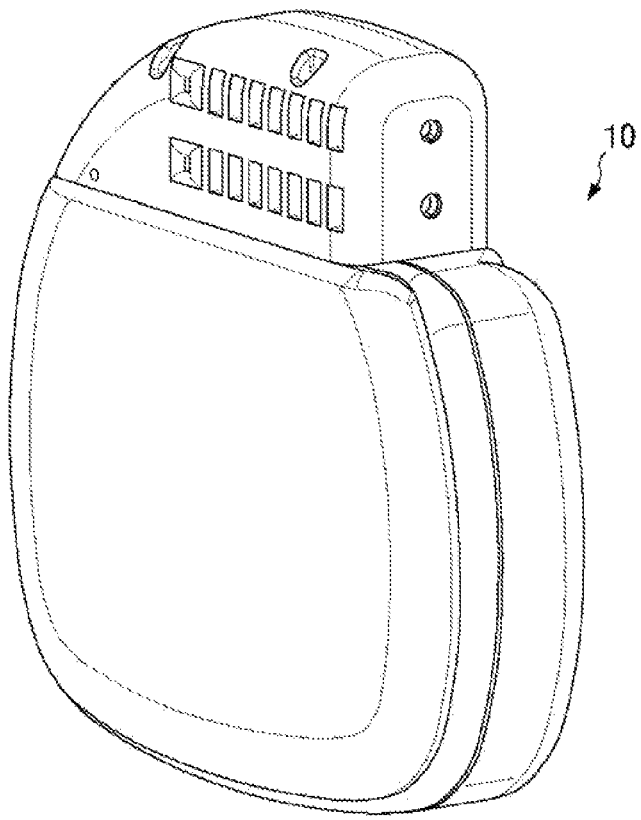
FIG. 1 illustrates an example implantable neurostimulation device.

FIG. 1 illustrates an example implantable neurostimulation device 10. In particular embodiments, implantable device 10 is an implantable pulse generator (IPG) including a power source (such as a battery) and electronics (such as hardware, software, or embedded logic components) for generating electrical stimulation pulses for transmission to nerve fibers or other anatomic structures in a patient for neurostimulation. Possible applications of implantable device 10 include treating chronic pain, treating neurological disorders, and treating motor dysfunctions. Although a particular implantable device 10 is illustrated and described, representative embodiments contemplate any suitable implantable device 10. As an example and not by way of limitation, in particular embodiments, implantable device 10 is an implantable receiver of a radio frequency (RF) neurostimulation system that, when implanted, receives power and electrical stimulation pulses from an transmitter located outside the body of the patient.

Figure 2:
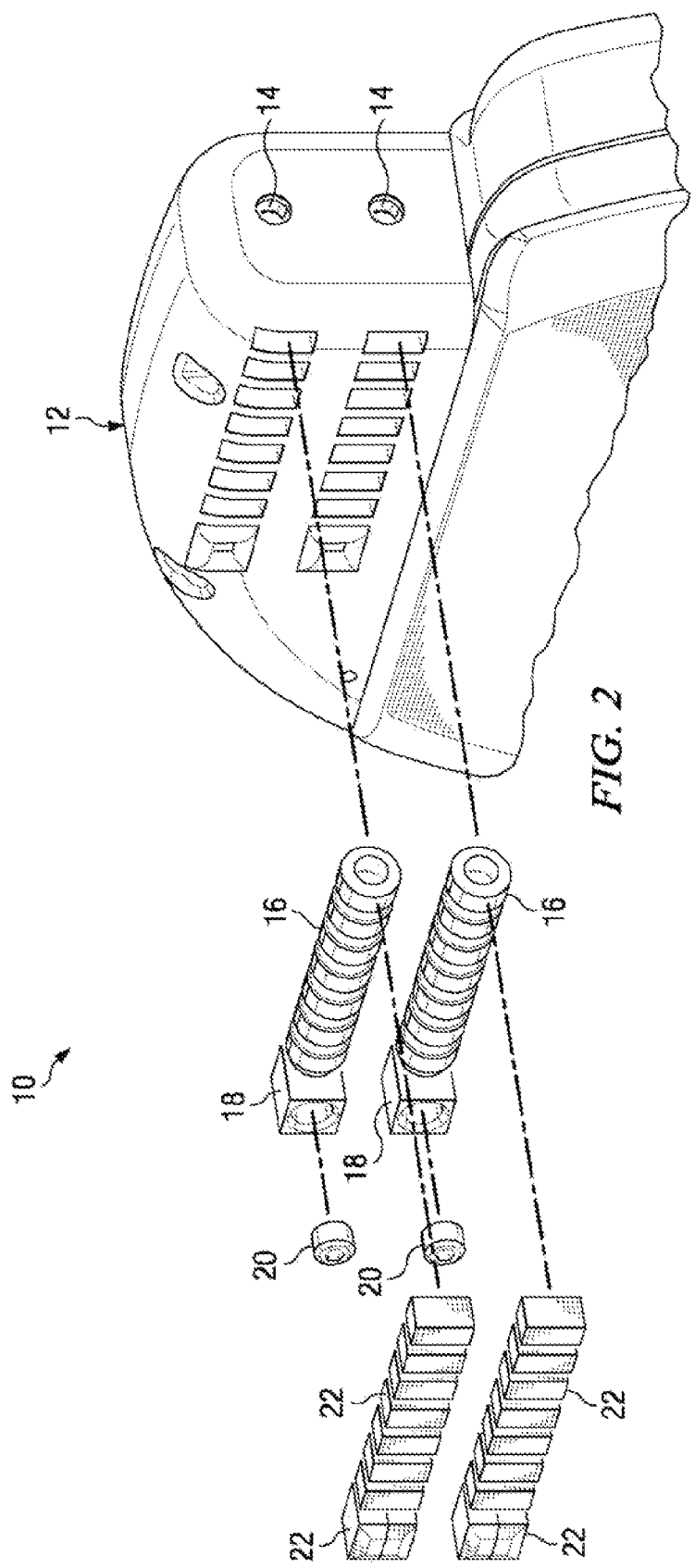
FIG. 2 illustrates an example header assembly of the example implantable neurostimulation device.

FIG. 2 illustrates an example header assembly 12 of implantable device 10. In particular embodiments, header assembly 12 includes electrical contacts corresponding to terminal electrodes located along the proximal end of a stimulation lead. The terminal electrodes are connected to corresponding stimulation electrodes located along the distal end of the stimulation lead via wires running through the stimulation lead. Electrical stimulation pulses are generated at implantable device 10 and transmitted through the electrical contacts, terminal electrodes, wires, and stimulation electrodes to the tissue to be stimulated. The stimulation electrodes deliver the stimulation pulses to nerve fibers or other anatomic structures according to placement of the stimulation electrodes within the body of the patient. As an example and not by way of limitation, in particular embodiments, the stimulation electrodes are placed to deliver the stimulation pulses to a portion of the spinal cord of the patient to treat chronic pain. Although header assembly 12 is illustrated as accommodating two stimulation leads each having eight stimulation electrodes, representative embodiments contemplate header assembly 12 accommodating any suitable number of stimulation leads (e.g., a single stimulation lead) each having any suitable number of stimulation electrodes (e.g., sixteen stimulation electrodes). For ease of understanding, a single stimulation lead is described unless otherwise indicated.

In particular embodiments, header assembly 12 receives a stimulation lead through an opening 14 and one or more housings 16 inside header assembly 12. A connector block 18 and a screw 20 inside header assembly 12 anchor the stimulation lead to header assembly 12. In particular embodiments, where stimulation lead includes eight terminal electrodes, header assembly 12 receives the stimulation lead through seven housings 16 and one connector block 18, as illustrated in FIG. 2. In a particular embodiment, connector block 18 is used to connect to the most proximal terminal electrode in a manner that more fully secures the stimulation lead to prevent the stimulation lead from separating from header assembly 12 while implanted in the patient. Although connector block 18 is illustrated and described, representative embodiments contemplate connector block 18 being omitted and a housing 16 to connect to each terminal electrode including the most distal terminal electrode. Plugs 22 cover housings 16 and connector blocks 18 and help hold housings 16 and connector blocks 18 in place inside header assembly 12. Housings 16 each provide electrical contact allowing stimulation pulses to travel from implantable device 10 through housings 16 to the terminal electrodes of the stimulation lead, as described below. To reduce an occurrence of oxidation, corrosion, or both on housing 16 adversely affecting electrical contact at housing 16, one or more portions of housing 16 may be made of platinum, an alloy of platinum, or another material resistant to oxidation and corrosion, as described below. Because such material is relatively expensive, housing 16 is a relatively expensive component of implantable device 10. To reduce material costs associated with housing 16 while retaining one or more benefits of using platinum, an alloy of platinum, or another relatively expensive material, such as resistance to oxidation and corrosion, according to representative embodiments only a portion of housing 16 is made of platinum, an alloy of platinum, or another relatively expensive material, as described below.

Figure 3:
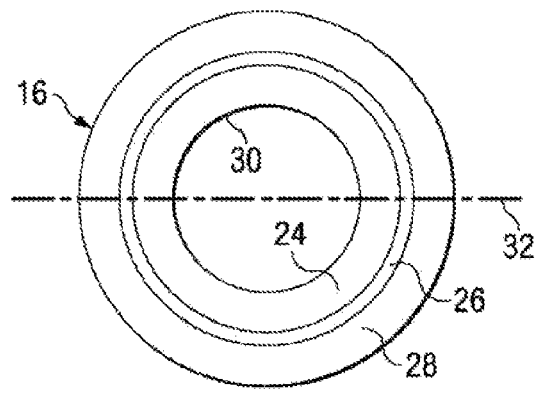
FIG. 3 illustrates an example housing for an electrical contact in the example implantable neurostimulation device.

FIG. 3 illustrates an example housing 16. In particular embodiments, housing 16 is a tube including an inner tubular portion 24, a middle tubular portion 26, and an outer tubular portion 28. In particular embodiments, housing 16 is constructed according to a cladding process well-known in the metal fabrication art. An inside of housing 16 defines a hole 30. Housing 16 receives a stimulation lead though hole 30. Plane 32 intersects housing 16.

In particular embodiments, inner tubular portion 24 and outer tubular portion 28 are made of stainless steel or a multiphase alloy of Nickel, Cobalt, Chromium, and Molybdenum (such as MP35N alloy). Inner tubular portion 24 and outer tubular portion 28 may be made of the same or different materials. Middle tubular portion 26 is made of platinum, an alloy of approximately 90% Platinum and approximately 10% iridium, or another material that is expensive relative to the material or materials that form inner tubular portion 24 and outer tubular portion 28. In contrast to previous housings 16 made entirely of platinum or a platinum alloy, in particular embodiments only middle tubular portion 26 of housing 16 contains the platinum, platinum alloy, or other relatively expensive material. As a result, material costs associated with housing 16 are less than if all or some of inner tubular portion 24, outer tubular portion 28, or both also contained platinum, a platinum alloy, or another relatively expensive material.

To achieve some but not all of the material cost benefits described above, outer tubular portion 24 may be made of stainless steel or another relatively inexpensive material and both middle tubular portion 26 and inner tubular portion 28 may be made of platinum, a platinum alloy, or another relatively expensive material. Similarly, to achieve some but not all of the material cost benefits described above, inner tubular portion 28 may be made of stainless steel or another relatively inexpensive material and both middle tubular portion 26 and outer tubular portion 24 may be made of platinum, a platinum alloy, or another relatively expensive material. Although a particular housing 16 including particular inner, middle, and outer tubular portions 24, 26, and 28, respectively, made of particular materials is illustrated and described, representative embodiments contemplate any suitable housing 16 including any suitable inner, middle, and outer tubular portions 24, 26, and 28, respectively, made of any suitable materials, provided one or more portions considered less critical for electrical contact are made of a material or materials that is inexpensive relative to a material or materials forming one or more portions considered more critical for electrical contact.

Figure 4:
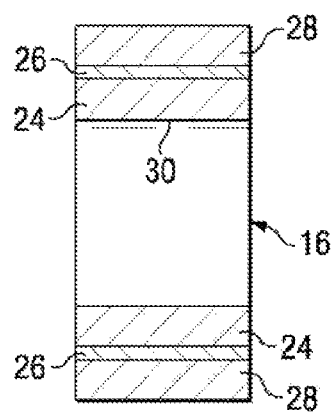
FIG. 4 illustrates a before-tooling cross-section of the example housing.
Figure 5:
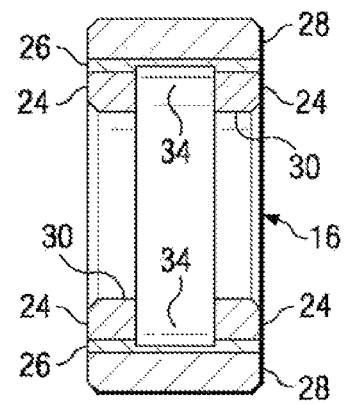
FIG. 5 illustrates an after-tooling cross-section of the example housing.

FIG. 4 illustrates a before-tooling cross-section of housing 16 through plane 32, and FIG. 5 illustrates an after-tooling cross-section of housing 16 through plane 32. Before tooling, middle tubular portion 26 of housing 16 is unexposed to hole 30. After tooling, groove 34 exposes middle tubular portion 26 of housing 16 to hole 30 to allow electrical contact between middle tubular portion 26 of housing 16 and a conductive object placed in groove 34 and therefore to allow stimulation pulses to travel from middle tubular portion 26 of housing 16 to a stimulation lead running through hole 30, as described below. In particular embodiments, a screw machine tools housing 16 to create groove 34 according to a screw machine process well-known in the metal tooling art. In addition, after tooling, edges on housing 16 may, but need not, be chamfered (or rounded), as illustrated in FIG. 5.

Figure 6:
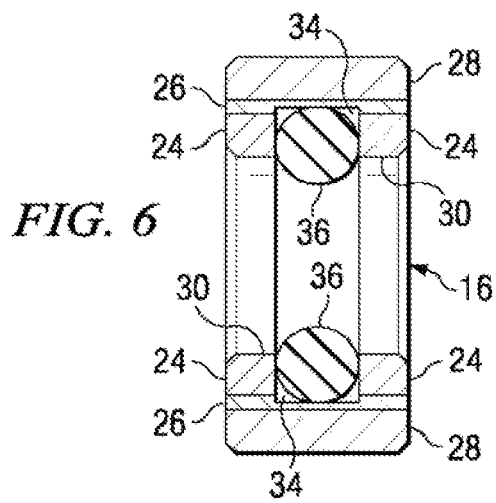
FIG. 6 illustrates a cross-section of the example housing including an example coiled spring.

FIG. 6 illustrates a cross-section, through plane 32, of housing 16 with an example coiled spring 34 lying in groove 34. In particular embodiments, coiled spring 34 is a canted, coiled spring 34. When housing 16 receives a stimulation lead though hole 30, coiled spring 34 is compressed between the stimulation lead and middle tubular portion 26 of housing 16 to secure the stimulation lead in housing 16 and to secure coiled spring 34 in groove 34. Coiled spring 34 transmits stimulation pulses from middle tubular portion 26 of housing 16 to the stimulation lead. Because in particular embodiments at least middle tubular portion 26 is made of platinum or an alloy of approximately 90% platinum and approximately 10% iridium, oxidation and corrosion are unlikely to impede electrical contact between housing 16 and coiled spring 34. Moreover, because in particular embodiments only a tubular portion of housing (e.g., only middle tubular portion 26) contains platinum, a platinum alloy, or another relatively expensive material, material costs associated housing 16 are less than if all or some of inner tubular portion 24, outer tubular portion 28, or both also contained such material.

Figure 7A:
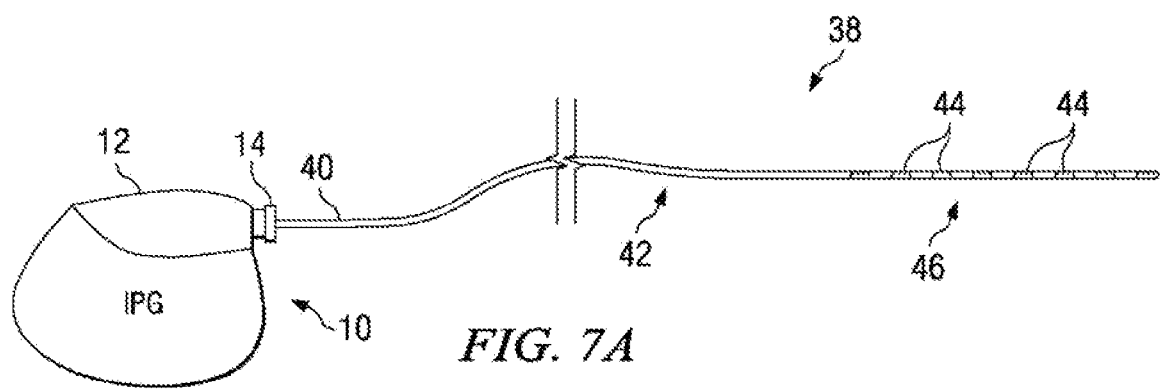
FIGS. 7A and 7B illustrate example implantable neurostimulation systems.
Figure 7B:
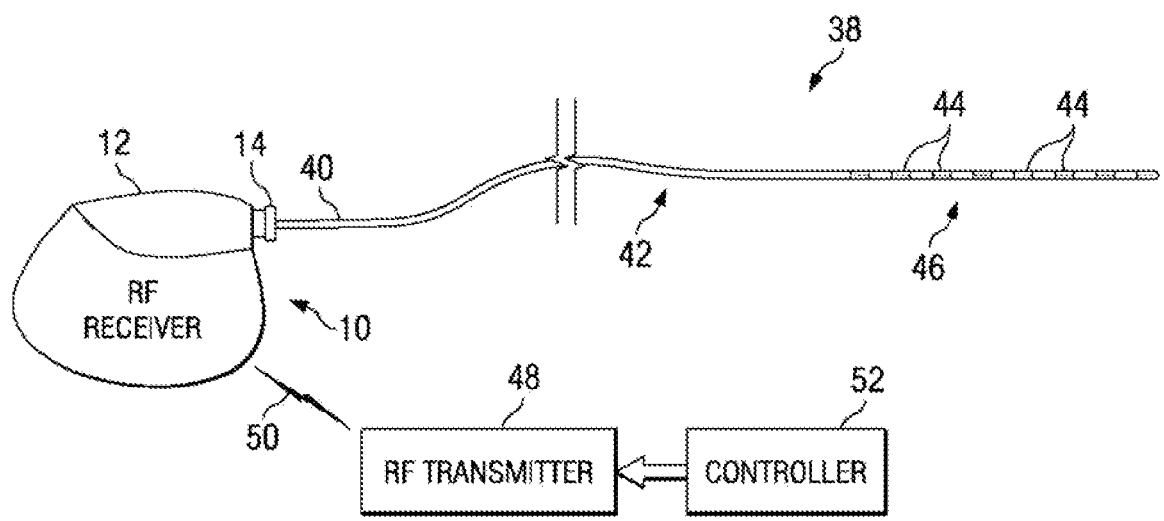

FIGS. 7A and 7B illustrate example implantable neurostimulation systems 38. Stimulation system 38 generates and applies a stimulus to a target area of the brain, the spinal cord, or a peripheral or other nerve. For example, a target area may be an area of the brain located in the cortex or, as a more particular example, in the primary auditory cortex to treat tinnitus. In general terms, stimulation system 38 includes an implantable neurostimulation device 12 and an implantable electrical stimulation lead 40 for applying the electrical stimulation pulses to target nerve tissue. In operation, both of these primary components are implanted in the person's body. Implantable neurostimulation device 12 is coupled to a connecting portion 42 of stimulation lead 40. Implantable neurostimulation device 12 controls the electrical stimulation pulses transmitted to electrodes 44 located on a stimulating portion 46 of stimulation lead 40, which is positioned on, in, near, or otherwise proximate the target nerve tissue, according to suitable stimulation parameters (e.g., duration, amplitude or intensity information, frequency information, etc.). A doctor, the patient, or another user of implantable neurostimulation device 12 may directly or indirectly input stimulation parameters to specify or modify the electrical stimulation provided.

Known neurostimulation devices can be adapted by utilizing a header assembly according to representative embodiments. In one embodiment, as shown in FIG. 7A, implantable neurostimulation device 12 includes an IPG. An example of a known IPG may be one manufactured by Advanced Neuromodulation Systems, Inc., such as the Genesis® System, part numbers 3604, 3608, 3609, and 3644. In another embodiment, as shown in FIG. 1B, implantable neurostimulation device 12 includes an implantable wireless receiver. An example of a known wireless receiver may be one manufactured by Advanced Neuromodulation Systems, Inc., such as the Renew® System, part numbers 3408 and 3416. The wireless receiver is capable of receiving wireless signals from a wireless transmitter 48 located external to the person's body. The wireless signals are represented in FIG. 1B by wireless link symbol 50. A doctor, the patient, or another user of implantable neurostimulation device 12 may use a controller 52 located external to the person's body to provide control signals for operation of implantable neurostimulation device 12. Controller 52 provides the control signals to wireless transmitter 48, wireless transmitter 48 transmits the control signals and power to the wireless receiver of implantable neurostimulation device 12, and implantable neurostimulation device 12 uses the control signals to vary the stimulation parameters of electrical stimulation pulses transmitted through stimulation lead 40 to the stimulation site. An example wireless transmitter 48 may be one manufactured by Advanced Neuromodulation Systems, Inc., such as the Renew® System, part numbers 3508 and 3516.

FIG. 8 illustrates an example method for reducing an amount of a contact material for an electrical stimulation lead contact in an implantable neurostimulation device. The method begins at step 100, where a middle tubular portion 26 of platinum, an alloy of approximately 90% platinum and approximately 10% iridium, or another relatively expensive material is clad with an inner tubular portion 24 and an outer tubular portion 28 of stainless steel, MP35N alloy, or another relatively inexpensive material to construct a housing 16. At step 102, a groove 34 is tooled into inner tubular portion 24 to expose middle tubular portion 26. At step 104, a coiled spring 34 is placed into groove 34. At step 106, housing 16 is placed into an implantable device 10. At step 108, before or during implantation of implantable device 10 into the body of a patient, a stimulation lead is inserted into housing 16 to electrically connect implantable device 10 to the stimulation lead, at which point the method ends. More specifically, in particular embodiments, housing 16 is electrically connected through coiled spring 34 to a corresponding terminal electrode of the stimulation lead, which is connected to a corresponding stimulation electrode of the stimulation lead via a corresponding wire running through the stimulation lead.

Although representative embodiments have been discussed in terms of neurostimulation devices, representative embodiments may provide a header assembly for any suitable stimulation device. For example, representative embodiments may provide a header assembly for spinal cord stimulation systems, deep brain stimulation systems, cortical stimulation systems, peripheral nerve stimulation systems, gastric pacing stimulation systems, functional stimulation systems, cardiac pacing stimulation systems, cardiac defibrillation systems, etc.

Although certain representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate when reading the present application, other processes, machines, manufacture, compositions of matter, means, methods, or steps, presently existing or later to be developed that perform substantially the same function or achieve substantially the same result as the described embodiments may be utilized. Accordingly, the appended claims are intended to include within their scope such processes, machines, manufacture, compositions of matter, means, methods, or steps.

The invention claimed is:

1. A tubular housing for electrically connecting an implantable medical device to an implantable electrical stimulation lead, the tubular housing comprising:
   a tubular outer segment comprising a first material;
   a tubular middle segment disposed inside the outer segment in contact with the outer segment and comprising a second material; and
   a tubular inner segment disposed inside the middle segment in contact with the middle segment and comprising a third material, a circumferential groove in the inner segment exposing a portion of the middle segment to an axial hole through the tubular housing, the groove adapted to receive a coiled spring, the groove enabling transmission of stimulation pulses from the exposed portion of the middle segment, through the coiled spring, to the stimulation lead inserted through the axial hole for stimulation of tissue in a patient.

2. The housing of claim 1, wherein the second material is different than the first and third materials and is expensive relative to the first and third materials.

3. The housing of claim 1, wherein:
the outer and inner segments comprise stainless steel or a multiphase alloy of Nickel, Cobalt, Chromium, and Molybdenum; and
the middle segment comprises platinum or an alloy of platinum and iridium.

4. The housing of claim 3, wherein the alloy of platinum and iridium comprises approximately 90% platinum and approximately 10% iridium.

5. The housing of claim 1, wherein the coiled spring is a canted, coiled spring.

6. The housing of claim 1, wherein the implantable stimulation device comprises an implantable pulse generator (IPG) or an implantable receiver of a radio frequency (RF) stimulation system.

7. The housing of claim 6, wherein an application of the implantable device comprises one or more of treating chronic pain, treating one or more neurological disorders, and treating one or more motor dysfunctions.

8. The housing of claim 1, wherein the tubular housing is constructed from the outer, middle, and inner segments according to a cladding process.

9. The housing of claim 1, wherein the groove is tooled into the inner segment according to a screw machine process.

10. An implantable stimulation device comprising:
circuitry for transmitting electrical stimulation pulses; and
a tubular housing for electrically connecting the circuitry of the implantable stimulation device to an implantable electrical stimulation lead, the tubular housing comprising:
a tubular outer segment comprising a first material;
a tubular middle segment disposed inside the outer segment in contact with the outer segment and comprising a second material; and
a tubular inner segment disposed inside the middle segment in contact with the middle segment and comprising a third material, a circumferential groove in the inner segment exposing a portion of the middle segment to an axial hole through the tubular housing, the groove adapted to receive a coiled spring, the groove enabling transmission of stimulation pulses from the exposed portion of the middle segment, through the coiled spring, to the stimulation lead inserted through the axial hole for stimulation of tissue in a patient.

11. The implantable stimulation device of claim 10, wherein the second material is different than the first and third materials and is expensive relative to the first and third materials.

12. The implantable stimulation device of claim 10, wherein:
the outer and inner segments comprise stainless steel or a multiphase alloy of Nickel, Cobalt, Chromium, and Molybdenum; and
the middle segment comprises platinum or an alloy of platinum and iridium.

13. The implantable stimulation device of claim 12, wherein the alloy of platinum and iridium comprises approximately 90% platinum and approximately 10% iridium.

14. The implantable stimulation device of claim 10, wherein the coiled spring is a canted, coiled spring.

15. The implantable stimulation device of claim 10, comprising an implantable pulse generator (IPG) or an implantable receiver of a radio frequency (RF) stimulation system.

16. The implantable stimulation device of claim 15, wherein an application of the implantable device comprises one or more of treating chronic pain, treating one or more neurological disorders, and treating one or more motor dysfunctions.

17. The implantable stimulation device of claim 10, wherein the tubular housing is constructed from the outer, middle, and inner segments according to a cladding process.

18. The implantable stimulation device of claim 10, wherein the groove is tooled into the inner segment according to a screw machine process.

19. An implantable stimulation device comprising:
circuitry for transmitting electrical stimulation pulses;
an implantable electrical stimulation lead; and
a tubular housing for electrically connecting the circuitry of the implantable stimulation device to the implantable electrical stimulation lead, the tubular housing comprising:
a tubular outer segment comprising a first material;
a tubular middle segment disposed inside the outer segment in contact with the outer segment and comprising a second material; and
a tubular inner segment disposed inside the middle segment in contact with the middle segment and comprising a third material, a circumferential groove in the inner segment exposing a portion of the middle segment to an axial hole through the tubular housing, the groove adapted to receive a coiled spring, the groove enabling transmission of stimulation pulses from the exposed portion of the middle segment, through the coiled spring, to the stimulation lead inserted through the axial hole for stimulation of tissue in a patient.

20. The implantable stimulation device of claim 19, wherein the second material is different than the first and third materials and is expensive relative to the first and third materials.

* * * * *

UNITED STATES PATENT AND TRADEMARK OFFICE
CERTIFICATE OF CORRECTION

PATENT NO.        : 7,567,842 B1
APPLICATION NO. : 11/536393
DATED              : July 28, 2009
INVENTOR(S)      : Terry D. Daglow and Stephen L. Goldman Page 1 of 1

It is certified that error appears in the above-identified patent and that said Letters Patent is hereby corrected as shown below:

On the title page, item (75) Inventor, add --Stephen L. Goldman, Frisco, TX (US)--.

Signed and Sealed this

Twenty-fourth Day of November, 2009

David J. Kappos
*Director of the United States Patent and Trademark Office*